United States Patent [19]

Sarges et al.

[11] 4,127,665
[45] Nov. 28, 1978

[54] THIENOHYDANTOIN DERIVATIVES

[75] Inventors: Reinhard Sarges, Mystic; Rodney C. Schnur, Noank, both of Conn.

[73] Assignee: Pfizer Inc., New York, N.Y.

[21] Appl. No.: 870,542

[22] Filed: Jan. 18, 1978

[51] Int. Cl.$^2$ .................. A01N 9/12; C07D 495/10
[52] U.S. Cl. ............................... 424/273 R; 548/309
[58] Field of Search ................... 548/309; 424/273 R

[56] References Cited
FOREIGN PATENT DOCUMENTS 1,135,915  9/1962  Fed. Rep. of Germany ........... 548/309

*Primary Examiner*—Richard Raymond
*Attorney, Agent, or Firm*—Francis X. Murphy; Charles J. Knuth; Peter C. Richardson

[57]  ABSTRACT

Novel spiro-thienohydantoin derivatives useful as aldose reductase inhibitors and as therapeutic agents for the treatment of chronic diabetic complications are disclosed. Preferred compounds include 6,7-dihydro-spiro-[benzo(b)thiophene-4(5H),4'-imidazolidine]-2',5'-dione, 2-chloro-spiro-[cyclopenta(b) thiophene-4,4'-imidazolidine]-2',5'-dione, spiro-[cyclopenta(c)thiophene-4,4'-imidazolidine]-2',5'-dione, 1-chloro-spiro[cyclopenta(c)thiophene-4,4'-imidazolidine]-2',5'-dione and 1,3-dichloro-spiro[cyclopenta(c)thiophene-4,4'-imidazolidine]-2',5'-dione.

20 Claims, No Drawings

THIENOHYDANTOIN DERIVATIVES

BACKGROUND OF THE INVENTION

This invention relates to novel spiro-thienohydantoin derivatives useful in the treatment of certain chronic complications arising from diabetes mellitus, such as diabetic cataracts and neuropathy, to pharmaceutical compositions containing such compounds and to a method of using these compounds. In the past various attempts have been made to obtain new and more effective oral antidiabetic agents. Generally, these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d, e]-isoquinoline-2(3H)-acetic acid and derivatives thereof to be useful for the treatment of these conditions, even though these particular compounds are not known to be hypoglycemic in nature. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way, unwanted accumulations of galactitol in the lens of galactosemic subjects and of sorbitol in the lens, peripheral nervous cord and kidney of various diabetic subjects are prevented or reduced. Accordingly, such compounds are of theraupeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel spiro-thienohydantoin derivatives of the formulae

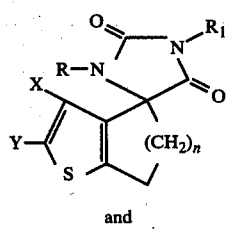

I and

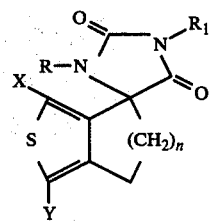

II and the base salts thereof with pharmaceutically acceptable cations, wherein R and $R_1$ are each selected from hydrogen, alkyl of 1 to 4 carbon atoms, benzyl and monosubstituted benzyl wherein said substituent is selected from hydroxyl, chloro, nitro and amino; X and Y are each selected from hydrogen, alkyl of 1 to 4 carbon atoms, chloro, bromo, fluoro, phenyl and monosubstituted phenyl, wherein said substituent is selected from hydroxyl, alkyl of 1 to 4 carbon atoms, alkoxyl of 1 to 4 carbon atoms, chloro, bromo, fluoro, nitro and amino; and $n$ is an integer from 1 to 3. Preferably, R and $R_1$ are each hydrogen, X and Y are either hydrogen or chloro and $n$ is either 1 or 2.

One group of compounds of interest is that of formula I. Preferred compounds of this formula are those wherein R and $R_1$ are each hydrogen, X and Y are each either hydrogen or chloro and $n$ is 1 or 2. Especially preferred compounds are 6,7-dihydrospiro[benzo(b)thiophene-4(5H),4'-imidazolidine]-2',5'-dione and 2-chloro-spiro[cyclopenta(d)thiophene-4,4'-imidazolidine]-2',5'-dione.

Also of interest are compounds of formula II, especially those compounds of this formula wherein R and $R_1$ are each hydrogen, X and Y are either hydrogen or chloro and $n$ is 1. Particularly preferred compounds are spiro[cyclopenta(c)thiophene-4,4'-imidazolidine]-2',5'-dione, 1-chloro-spiro[cyclopenta(c)thiophene-4,4'-imidazolidine]-2',5'-dione and 1,3-dichloro-spiro [cyclopenta(c)thiophene-4,4'-imidazolidine]-2',5'-dione.

The present invention further comprises a novel method for the treatment of a diabetic host to prevent or alleviate diabetes-associated complications, such as cataracts, neuropathy or retinopathy, which method comprises administering to the host an effective amount of a compound of formulae I or II. Further disclosed is a pharmaceutical composition comprising a pharmaceutically-acceptable carrier and a compound of formulae I or II in an amount effective to prevent or alleviate diabetes-associated complications, such as cataracts, neuropathy or retinopathy.

DETAILED DESCRIPTION OF THE INVENTION

The novel compounds of the present invention are readily prepared from an appropriate ketone of the formula

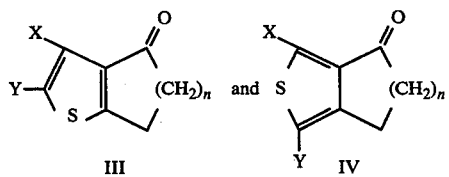

III    IV wherein X, Y and $n$ are as previously defined. Ketones of formula III are starting materials for spiro-thienohydantoins of formula I, while compounds of formula IV are starting materials for the novel compounds of formula II. An appropriately substituted ketone of formulae III or IV is condensed with an alkali metal cyanide, such as sodium cyanide or potassium cyanide, and ammonium carbonate for form the desired spirothienohydantoin of formulae I or II, respectively. The reaction is normally conducted in the presence of a reaction-inert polar organic solvent in which both the reactants and reagents are mutually miscible. Preferred organic solvents include, but are not limited to, cyclic ethers such as dioxane and tetrahydrofuran, lower alkylene glycols such as ethylene glycol and trimethylene glycol, water-miscible lower alkanols such as methanol, ethanol and isopropanol, and N,N-di(lower alkyl) lower alkanoamides such as N,N-dimethyl formamide, N,N-diethyl formamide and N,N-dimethyl acetamide. In general, the reaction is conducted at a temperature between about 50° C. and about 150° C., preferably about 90° C. to 130° C., for a period of about 2 hours to about 4 days, depending on the temperature employed. Although the amount of reactants and reagents employed in the reaction can vary to some extent, it is preferable to employ at least a slight molar excess of the alkali metal cyanide reagent with respect to the ketone starting material in order to effect maximum yield. Upon completion of the reaction, the desired product is readily isolated in a conventional manner, for example by first diluting the reaction mixture with water and then cooling the resultant aqueous solution to room temperature, followed by acidification to afford the desired spiro-thienohydantoin compound in the form of a readily-recoverable precipitate. Production of compounds of formulae I and II wherein R and $R_1$ are alkyl, benzyl or substituted benzyl is effected by further reacting those compounds where R and $R_1$ are hydrogen to introduce the desired substituent, using alkylation reactions well known in the art.

The starting materials of formulae III and IV are readily prepared from appropriately 2,3- and 2,5-substituted thiophenes according to the procedures described by MacDowell et al., J. Org. Chem., 32, 1226 (1967) and by Muraro et. al., Bull. Soc. Chim. Fr. 1973, 335 (1973). In accord with these procedures, the substituents X and Y are preferably present in the thiophene reactant used in this reaction. However, it is also possible to prepare compounds of formulae III and IV by introducing the substituents X and Y by known reactions with the corresponding unsubstituted compound (i.e., the compounds of formulae III and IV wherein either or both X and Y are hydrogen). For example, compounds wherein X or Y are halogen can be prepared from the corresponding unsubstituted compounds by direct halogenation techniques well known in the art. Other desired substituents X and Y may likewise be obtained from appropriate reactants by known methods.

Pharmaceutically acceptable base salts can be readily prepared from compounds of formulae I and II wherein $R_1$ is hydrogen by conventional methods. Thus, these salts may be readily prepared by treating such spiro-thieno-hydantoins with an aqueous solution of the desired pharmaceutically acceptable cation and evaporating the resulting solution to dryness, preferably under reduced pressure. Alternatively, a lower alkanoic solution of the spiro-thienohydantoin may be mixed with an alkoxide of the desired metal and subsequently evaporating the solution to dryness. By pharmaceutically acceptable cations is meant those cations that form base salts with acidic compounds of formulae I and II which are non-toxic at the dosages administered to a subject in need of treatment. Suitable cations for this purpose include, but are not limited to, potassium, sodium, ammonium, calcium and magnesium.

The novel spiro-thienohydantoins of this invention are useful as aldose reductase inhibitors, and as such are of therapeutic value in the treatment of chronic complications of diabetes, such as cataracts, retinopathy and neuropathy. As used in the claims and specification hereof, treatment is meant to include both prevention or alleviation of such conditions. The compounds may be administered to a subject in need of treatment by a variety of conventional routes of administration, including orally and parenterally. In general, these compounds will be administered at dosages between 1 and 250 mg per kg body weight of the subject to be treated per day. However, some variation in dosage will necessarily occur depending on the condition of the subject being treated and the physician will, in any event, determine the appropriate dose of the invidiual subject.

The compounds may be administered alone or in combination with pharmaceutically acceptable carriers, in either single or multiple doses. Suitable pharmaceutical carriers include inert solid diluents or fillers, sterile aqueous solutions and various non-toxic organic solvents. The pharmaceutical compositions formed by combining the spiro-thienohydantoin and the pharmaceutically acceptable carrier are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes, and if desired emulsifying or suspending agents, together with diluents such as water, ethanol, propylene glycol, glycerin and combinations thereof.

For parenteral administration, solutions of the spiro-thienohydantoins in sesame or peanut oil or in aqueous propylene glycol may be employed, as well as sterile aqueous solutions of the corresponding water-soluble alkali metal or alkaline-earth metal salts previously described. Such aqueous solutions should be suitably buffered if necessary and the liquid diluent first rendered isotonic with sufficient saline or glucose. These particular aqueous solutions are especially suitable for intraveneous, intramuscular, subcutaneous and intraperitoneal injection purposes. In this connection, the sterile aqueous media employed are all readily obtainable by standard techniques well known to those skilled in the art. Additionally, it is also possible to administer the spiro-thienohydantoin compounds topically, by use of an appropriate opthalmic solution, which may then be administered dropwise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats.

The present invention is illustrated by the following examples. It will be understood, however, that the invention is not limited to the specific details of these examples.

EXAMPLE 1

1,3-Dichloro-spiro[cyclopenta(c)thiophene-4,4'-imidazolidine]-2', 5'-dione

A mixture of 0.900 g (4.30 mmol) of 1,3-dichloro-cyclopenta(c) thiophene-4-one (MacDowall et. al., J. Org. Chem., 32, 1226 (1967) 0.488 g (7.50 mmol) of potassium cycnide and 3.30 g (34 mmol) of powdered ammonium carbonate were heated with 25 ml of 50% aqueous ethanol at 110°–120° C. in a steel bomb for 16 hours. The reaction mixture was cooled, diluted with 200 ml of water, boiled for 10 to 15 minutes, then cooled and extracted with ethyl acetate. The organic layer was washed with brine, dried over sodium sulfate, filtered and evaporated in vacuo to a tan solid (0.980 g) which was crystallized from ethyl acetate to give 0.600 g (50%) of 1,3-dichloro-spiro[cyclopenta(c)thiophene-4,4'-imidazolidine]-2',5'-dione, mp 239°–241° C.

Analysis: Calcd. for $C_9H_6Cl_2N_2O_2S$: C, 39.00%; H, 2.18%, N; 10.11%.

Found: C, 39.21%; H, 2.13%; N, 10.05%.

EXAMPLE 2

1-Chloro-spiro[cyclopenta(c)thiophene-4,4'-imidazolidine]-2',5'-dione

The procedure described in Example 1 was repeated using 1-chloroctclopenta(c)thiophene-4-one (Muraro et. al., Bull. Soc. Chim. Fr. 1973, 335) as starting material. 1-chloro-spiro[cyclopenta(c)thiophene-4,4'-imidazolidine]-2',5'-dione was obtained in 25% yield, mp 224°–225° C.

Analysis: Calcd. for $C_9H_7ClN_2OS$: C, 44.54%; H, 2.91%; N, 11.54%.

Found: C, 45.05%; H, 3.13%; N, 11.20%.

EXAMPLE 3

Spiro[cyclopenta(c)thiophene-4,4'-imidazolidine]-2',5'-dione

The procedure of Example 1 was repeated using cyclopenta(c)thiophene-4-one (MacDowell et. al., supra) as starting material and at a reaction temperature of 80°–90° C. Spiro[cyclopenta(c)thiophene-4,4'-imidazolidine]-2',5'-dione was obtained in 38% yield, mp 241°–243° C.

Anaylsis: Calcd. for $C_9H_8N_2O_2S$: C, 51.91%, H, 3.87%, N, 13.45%.

Found: C, 51.95%; H, 3.93%; N, 13.34%.

EXAMPLE 4

2-Chloro-spiro[cyclopenta(b)thiophene-4,4'-imidazolidine]-2',5'-dione

Sulfuryl chloride (2.5 ml) was added to 4.7 g (0.030 mol) of 3-(2-thienyl) propionic acid (K&K) dissolved in 2 ml of carbon tetrachloride during 20 minutes. After an additional 1 hour at room temperature, the mixture was poured into 50–100 ml ether and extracted with 50–100 ml water and 3 times with 50–100 ml saturated sodium chloride, dried over sodium sulfate and evaporated in vacuo to a dark oil. 3-(5-chloro-2-thienyl) propionic acid was recrystallized from hexane to give 2.40 g, 42%, mp 46°–48° C.

Analysis: Calcd. for $C_7H_7ClO_2S$: C, 44.10%; H, 3.70%.

Found: C, 44.33%; H, 3.86%.

Following the procedure of MacDowell, supra, 2-chloro-cyclopenta (b)thiophene-4-one was obtained from 3-(5-chloro-2-thienyl) propionic acid in 62% yield, mp 99°–101° C.

Analysis: Calcd. for $C_7H_5ClOS$: C, 48.70%; H, 2.92%.

Found: C, 49.01%; H, 3.13%.

The procedure of Example 1 was then repeated using 2-chlorocyclopenta(b)thiophene-4-one as starting material and a reaction temperature of 130° C. 2-chloro-spiro[cyclopenta(b)thiophene-4,4'-imidazolidine]-2',5'-dione in 32% yield, mp 270°–271° C.

Analysis: Calcd. for $C_9H_7ClN_2O_2S$: C, 44.54%; H, 2.91%; N, 11.54%.

Found: C, 44.68%; H, 2.90%; N, 11.44%.

EXAMPLE 5

6,7-Dihydro-spiro[benzo(b)thiopheen-4(5H),4'-imidazolidine]-2',5'-dione

The procedure of Example 1 was repeated using 6,7-dihydro-benzo (b) thiophene-4(5H) -one (Aldrich) as starting material and a reaction temperature of 110° C. 6,7-dihydro-spiro[benzo(b)thiophene-4(5H),4'-imidazolidine]-2',5'-dione was obtained in 52% yield, mp 265.5°–268° C.

Analysis: Calcd. for $C_{10}H_{10}N_2O_2S$: C, 54.03%; H, 4.53%; N, 12.61%.

Found: C, 53.87%; H, 4.49%; N, 12.53%.

EXAMPLE 6

The spiro-thienohydantoins of Examples 1 through 5 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-4}M$ are expressed as percent inhibition of enzyme activity.

| Compound of | % Inhibition at $10^{-4}M$ |
|---|---|
| Example 1 | 83 |
| Example 2 | 95 |
| Example 3 | 46 |
| Example 4 | 80 |
| Example 5 | 52 |

EXAMPLE 7

The test of Example 6 was repeated at different concentrations of the compound under test, namely $10^{-4}M$, $10^{-5}M$, $10^{-6}M$, and $10^{-7}M$.

| Compound of | % Inhibition | | | |
|---|---|---|---|---|
| | $10^{-4}$M | $10^{-5}$M | $10^{-6}$M | $10^{-7}$M |
| Example 1 | 88 | 67 | 12 | −7 |
| Example 2 | 35 | 67 | −12 | 21 |
| Example 4 | 75 | 55 | 18 | 15 |

In this test, values below 20 are not always experimentally and statistically significant. Likewise, the low negative values shown, while suggesting a stimulation rather than an inhibition at low concentrations, are not considered experimentally significant.

EXAMPLE 8

The compounds of Examples 4 and 5 were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50–100 mM/g. tissue to as high as 400 mM/g. tissue in the 27-hour test period):

| Compound of | % Inhibition | |
|---|---|---|
| | 2.5 mg/kg | 25 mg/kg |
| Example 4 | 20 | — |
| Example 5 | — | 56 |

What is claimed is:

1. A compound selected from those of the formulae:

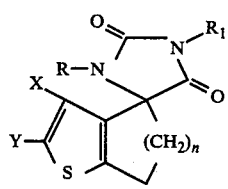

I and

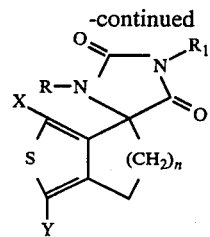

II and the base salts thereof with pharmaceutically acceptable cations, wherein R and $R_1$ are each selected from hydrogen, alkyl of 1 to 4 carbon atoms, benzyl and monosubstituted benzyl wherein said substituent is selected from hydroxyl, chloro, nitro and amino;

X and Y are each selected from hydrogen, alkyl of from 1 to 4 carbon atoms, chloro, bromo, fluoro, phenyl and monosubstituted phenyl wherein said substituent is selected from hydroxyl, alkyl of 1 to 4 carbon atoms, alkoxyl of 1 to 4 carbon atoms, chloro, bromo, fluoro, nitro and amino;

and n is an integer from 1 to 3.

2. A compound of claim 1 wherein R and $R_1$ are each hydrogen.
3. A compound of claim 1 wherein X and Y are each selected from hydrogen and chloro.
4. A compound of claim 1 wherein n is 1.
5. A compound of claim 1 wherein n is 2.
6. A compound of claim 1, formula I.
7. A compound of claim 6, wherein R and $R_1$ are each hydrogen.
8. A compound of claim 7 wherein X and Y are each hydrogen.
9. A compound of claim 8 wherein n is 2.
10. A compound of claim 7 wherein X is hydrogen and Y is chloro.
11. A compound of claim 10 wherein n is 1.
12. A compound of claim 1, formula II.
13. A compound of claim 12 wherein R and $R_1$ are each hydrogen.
14. A compound of claim 13, wherein X and Y are each hydrogen.
15. A compound of claim 14 wherein n is 1.
16. A compound of claim 13 wherein X and Y are each selected from hydrogen and chloro.
17. A compound of claim 16 wherein X is chloro, Y is hydrogen and n is 1.
18. A compound of claim 16 wherein X and Y are each chloro and n is 1.
19. A method of treating a diabetic host for diabetes-associated complications, which comprises administering to said host an effective amount of a compound of claim 1.
20. A pharmaceutical composition comprising a pharmaceutically-acceptable carrier and a compound of claim 1 in an amount effective for the treatment of diabetes-associated complications.

* * * * *